(12) United States Patent
Gitlin et al.

(10) Patent No.: US 8,358,981 B1
(45) Date of Patent: Jan. 22, 2013

(54) MINIMALLY INVASIVE NETWORKED SURGICAL SYSTEM AND METHOD

(75) Inventors: Richard Gitlin, Tampa, FL (US); Craig Lusk, Lutz, FL (US); Shekhar Bhansali, Tampa, FL (US); Alexander Rosemurgy, Tampa, FL (US)

(73) Assignee: University of South Florida, Tampa, FL (US)

( * ) Notice: Subject to any disclaimer, the term of this patent is extended or adjusted under 35 U.S.C. 154(b) by 288 days.

(21) Appl. No.: 12/608,580

(22) Filed: Oct. 29, 2009

Related U.S. Application Data

(60) Provisional application No. 61/109,368, filed on Oct. 29, 2008.

(51) Int. Cl.
*H04B 7/00* (2006.01)
*H04M 1/00* (2006.01)
(52) U.S. Cl. .................................. 455/66.1; 455/575.6
(58) Field of Classification Search ................. 455/66.1, 455/67.11, 575.6, 569.1, 100, 41.1, 41.2, 455/41.3; 607/60, 3
See application file for complete search history.

(56) References Cited

U.S. PATENT DOCUMENTS

| | | | |
|---|---|---|---|
| 5,604,531 A | 2/1997 | Iddan et al. | |
| 6,402,689 B1 | 6/2002 | Scarantino et al. | |
| 6,546,272 B1 | 4/2003 | MacKinnon et al. | |
| 7,009,634 B2 | 3/2006 | Iddan et al. | |
| 7,214,182 B2 | 5/2007 | Shimizu et al. | |
| 2006/0009818 A1* | 1/2006 | Von Arx et al. | 607/60 |
| 2007/0255098 A1 | 11/2007 | Wang et al. | |
| 2007/0270651 A1 | 11/2007 | Gilad et al. | |

OTHER PUBLICATIONS

Hu, et al., In-Vivo Pan/Tilt Endoscope with Integrated Light Source, IEEE/RSJ International Conference on Intelligent Robots and Systems, 2007.

* cited by examiner

*Primary Examiner* — Eugene Yun
(74) *Attorney, Agent, or Firm* — Nilay J. Choksi; Courtney M. Dunn; Smith & Hopen, P.A.

(57) ABSTRACT

A system for performing non-invasive networked medical procedures including a number of in vivo medical devices, a communication path between at least two of the devices, an ex vivo control unit to control the behavior of the devices, and a wireless communication path between the control unit and at least one of the devices. An associated method for performing non-invasive networked medical procedures is also provided.

15 Claims, 1 Drawing Sheet

MINIMALLY INVASIVE NETWORKED SURGICAL SYSTEM AND METHOD

CROSS REFERENCE TO RELATED APPLICATIONS

This application claims priority to currently pending U.S. Provisional Patent Application No. 61/109,368, entitled, "Non-Invasive Networked Surgery", filed Oct. 29, 2008.

FIELD OF INVENTION

This invention relates to a system and method device for minimally invasive surgical procedures; more specifically a network of various in vivo medical devices.

BACKGROUND

As minimally invasive surgical (MIS) procedures become increasing sophisticated, new functions will be needed to realize successful surgical outcomes. For example, conventional laparoscopy places a limit on the number of devices that can be inserted in the body. In addition, these devices have limited positioning capabilities and may compete or interfere with the preferred motion or position of another instrument.

Devices and methods for performing in vivo imaging of passages or cavities within a body are known in the art, and there are self-propelled devices known in the art. However, these conventional technologies use a single device (e.g. a camera pill), which are difficult to inject into the body and properly position and navigate due to their size. Having a single device also limits the ability of the surgeon to perform multiple tasks in a single session, or view the progress of the surgical procedure from the most advantageous angle.

SUMMARY

The present invention includes a system and associated method for performing minimally invasive, networked medical procedures. The system includes a number of in vivo medical devices, such as imaging devices, sensors, power sources, and cutting tools, and a communication path between at least two of the in vivo medical devices. The system further includes an ex vivo control unit to control the behavior of the in vivo medical devices and a wireless communication path between the control unit and at least one of the in vivo medical devices. The system may further include a second wireless communication path between at least one of the in vivo medical devices and an ex vivo system.

The communications and control units may be combined into a single unit and their communications paths may be shared. The in vivo medical devices may be electronically addressable and electronically controllable. The in vivo medical devices may also be magnetically controllable. There also may be a number of wireless communication paths between the control unit and each of the in vivo medical devices. These wireless communications links, or additional wireless links, also provide a two-way communication path for the in-vivo devices to communicate a variety of information with external systems.

The method of performing networked medical procedures includes providing a number of in vivo medical devices and a communication between at least two of the in vivo medical devices. The method further includes providing an ex vivo control unit to control the behavior of the in vivo medical devices and providing a wireless communication path between the control unit and at least one of the in vivo medical devices. The method also includes controlling the behavior of the in vivo medical devices from outside the body using the wireless communication path between the control unit and the at least one of the in vivo medical devices. The method may further include providing a second wireless communication path between at least one of the in vivo medical devices and an ex vivo system. The second wireless communication path may be a duplex wireless communication path.

Controlling the behavior of the in vivo medical devices from outside the body using the wireless communication path between the control unit and at least one of the in vivo medical devices may include generating a control signal at the control unit and transmitting the control signal over the wireless communication path to a first in vivo medical device. Controlling the behavior of the in vivo medical devices from outside the body may also include receiving the control signal at the first in vivo medical device, generating a second control signal at the first in vivo medical device, and transmitting the second control signal over the communication path between the first in vivo medical device and a second in vivo medical device to the second in vivo medical device.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
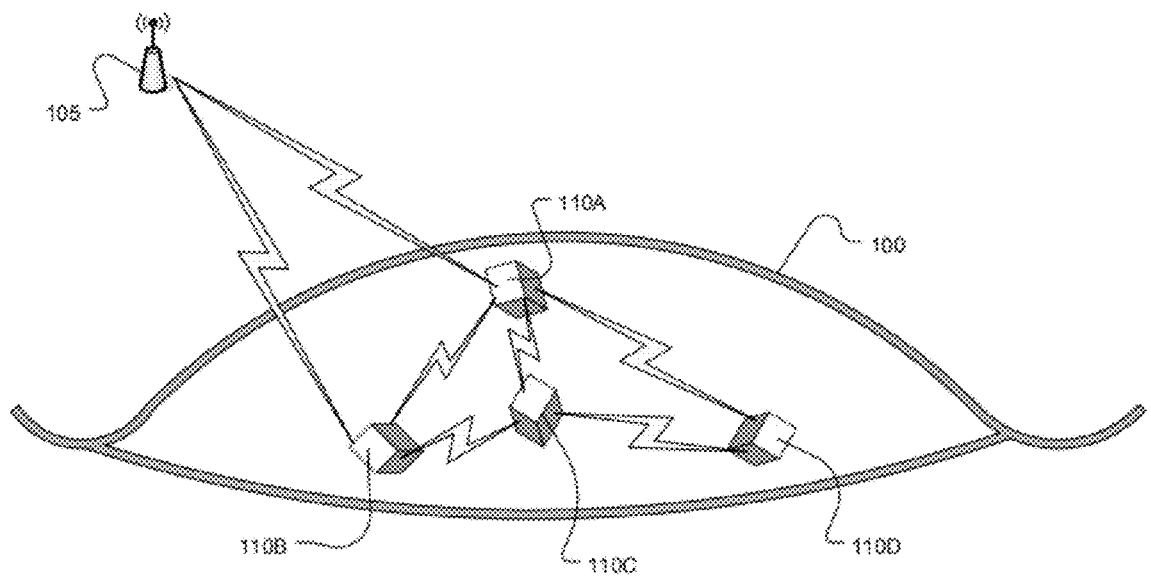
FIG. 1 is a general diagram of a plurality of in vivo medical devices, which are networked together and controlled wirelessly via a wireless access point located outside the body, in accordance with an embodiment of the present invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention includes a system and associated method for performing noninvasive medical procedures. The system includes a number of networked devices for in vivo medical applications. The term "in vivo" as used herein refers to being inside of a living organism or cell. Thus, for example, a medical device that is in vivo can be found inside of the subject organism or cell. Typical applications include but are not limited to procedures in the gastrointestinal tract of a human being. The system and method allow for the performance of complex and time-consuming surgeries to be minimally invasive and in some cases with only local or no anesthesia. This increases the safety of the surgery and minimizes patient anxiety.

The invention includes a plurality of in vivo medical devices of the same or different types, such as imaging devices, sensors, power sources, collectors, and "cutting" tools (physical, optical, ultrasound, lasers, etc.). There also may be multiples of the same type of device. For example, multiple batteries may be used so that the devices do not prematurely run out of power.

The devices are controlled by one or more external (ex vivo) control units, such as an expert system. The invention may include other external (ex vivo) systems in addition to the control unit. The term "ex vivo" as used herein refers to being outside of a living organism. Thus, for example, a system that is ex vivo can be found outside of the subject organism. Examples of such an external system include a server and an external display system for displaying images from an in vivo video camera. The invention may further include one or more external (ex vivo) communication units, such as an external wireless access point, which transmit data between the in vivo medical devices and the one or more external control units or other external systems.

The invention may also include one or more communication paths between one or more of the in vivo medical devices and the external system(s). These communication paths may carry control signals or any other type of communication required by the system. The communication path may either be a separate communications link with dedicated resources (e.g. separate frequency, time slot, or code, for each "path") or an addressable logical link in a shared medium (such as a packet network). Each communication path may be uni- or bi-directional depending on the needs of the system. For example, an in vivo video camera may have a dedicated communication path between it and an external control and display system. The control signal would be sent from the external system to the video camera via the communication path and the camera would send images to the external system via the same communication path. Alternatively, there may be more than one communication path between two devices— one carrying control signals and another for communication.

The invention may also include one or more communication paths between the in vivo medical devices. These communication paths may carry control signals or any other type of communication required by the system. The communication paths may also relay information received by one in vivo medical device from an external system to another in vivo medical device. Each communication path may be uni- or bi-directional depending on the needs of the system.

Each of the devices may be externally electronically addressable. Each device may be externally controllable (e.g., via wireless, magnetic, or other means). Each device may perform a required task in response to externally generated control signals. The device may be positioned in response to the control commands. Movement of the devices may be accomplished in a variety of ways including mini motors and thrusters, as well as the use of magnets. The devices may have means of acquiring position or other information (e.g., a GPS). The devices may be capable of originating communications with the external systems or with other in vivo devices. These communications may, for example, communicate the information acquired by the device and/or the status or condition of the device.

The devices may assume a hierarchical, mesh, tree, ad-hoc, or other architecture that is appropriate for the application.

A generalized example of the present invention is shown in FIG. 1. In this example, plurality of in vivo medical devices 110A-110D are networked together and controlled wirelessly via wireless access point 105 located outside body cavity 100.

Figure 2:
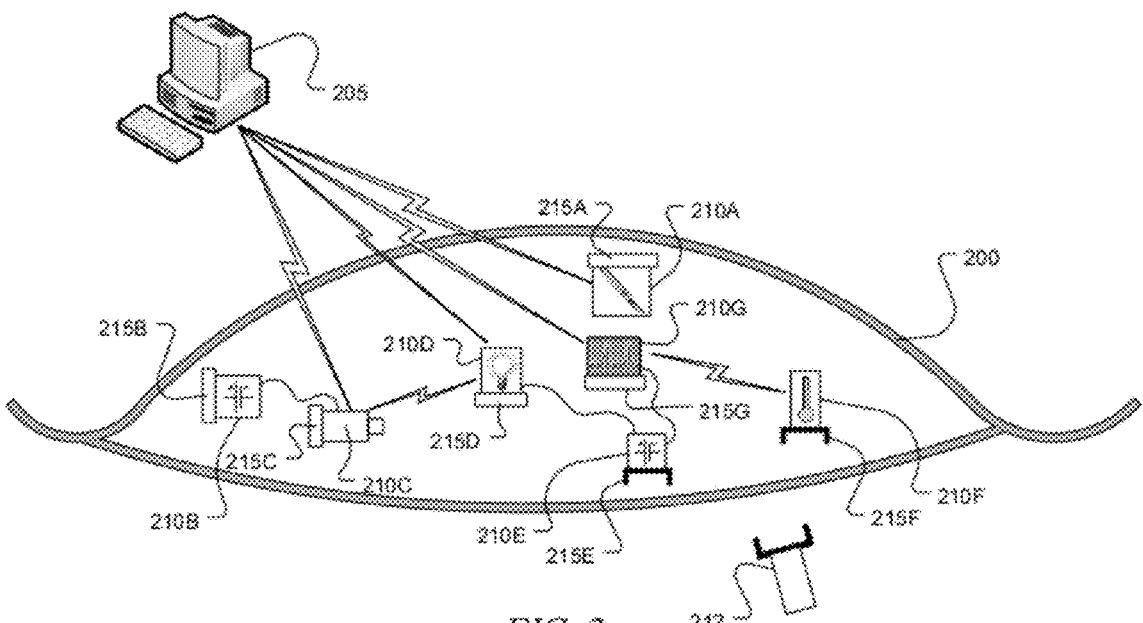
FIG. 2 is a diagram of a plurality of exemplary in vivo medical devices, which are networked together and controlled wirelessly by a control unit located outside the body, in accordance with an embodiment of the present invention.

Another example is shown in FIG. 2. Here, the in vivo medical devices include cutting tool 210A with positioning device 215A, battery 210B with positioning device 215B, camera 210C with positioning device 215C, light 210D with positioning device 215D, battery 210E with magnet 215E, sensor 210F with magnet 215F, and monitor 210G with positioning device 215G. Positioning devices include any device that provides movement to the respective in vivo medical device, such as mini-motors or thrusters. In addition, external magnet 212 may be used in conjunction with magnet 215E or 215F to move battery 210E or sensor 210F, respectively.

In vivo medical devices 210A-210G may be connected to one or more of each other via a wired or wireless connection. For example, in FIG. 2, camera 210C has a wired connection with battery 215B and a wireless connection with light 210D. Further, any number of in vivo medical devices 210A-210G may be wirelessly connected to an external control unit, here computer 205. In this example, four in vivo medical devices are wirelessly connected to computer 205—cutting tool 210A, camera 210C, light 210D, and monitor 210G.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between

What is claimed is:

1. A system for performing networked medical procedures comprising:
    a plurality of in vivo medical devices;
    a network providing a communication path between at least two of the plurality of in vivo medical devices, said network comprising a Layer 3 data network;
    an ex vivo control unit to control the behavior of the plurality of in vivo medical devices, said behavior including spatial parameters of said plurality of in vivo medical devices;
    said network providing a wireless communication path between the control unit and at least one of the plurality of in vivo medical devices.

2. The system of claim 1, further comprising:
    a second wireless communication path between at least one of the plurality of in vivo medical devices and an ex vivo system.

3. The system of claim 1, wherein the control unit is a magnet.

4. The system of claim 1, wherein the control unit is an electronic device that generates control signals.

5. The system of claim 1, wherein the control unit is an electronic device that generates communication signals.

6. The system of claim 1, wherein each of the plurality of in vivo medical devices are one or more medical devices chosen from the group consisting of an imaging device, a sensor, a power source, and a cutting tool.

7. The system of claim 1, wherein the communication path between the at least two in vivo medical devices is wireless.

8. The system of claim 1, wherein the communication path between the at least two in vivo devices is wired.

9. The system of claim 1, wherein each of the plurality of in vivo medical devices is separately wirelessly addressable and controllable.

10. The system of claim 1, further comprising:
    a plurality of wireless communication paths between the control unit and each of the plurality of in vivo medical devices.

11. A method of performing networked medical procedures comprising:
    providing a plurality of in vivo medical devices;

establishing a network that provides a communication path between at least two of the plurality of in vivo medical devices, said network comprising a Layer 3 data network;

providing an ex vivo control unit to control the behavior of the plurality of in vivo medical devices, said behavior including spatial parameters of said plurality of in vivo medical devices;

said network providing a wireless communication path between the control unit and at least one of the plurality of in vivo medical devices; and controlling the behavior of the plurality of in vivo medical devices from outside the body using the wireless communication path between the control unit and the at least one of the plurality of in vivo medical devices.

12. The method of claim 11, further comprising:

providing a second wireless communication path between at least one of the plurality of in vivo medical devices and an ex vivo system.

13. The method of claim 12, wherein the second wireless duplex communication path is a duplex communication path.

14. The method of claim 11, wherein controlling the behavior of the plurality of in vivo medical devices from outside the body using the wireless communication path between the control unit and the at least one of the plurality of in vivo medical devices, comprises:

generating a control signal at the control unit; and transmitting the control signal over the wireless communication path to a first in vivo medical device of the plurality of in vivo medical devices.

15. The method of claim 14, wherein controlling the behavior of the plurality of in vivo medical devices from outside the body using the wireless communication path between the control unit and the at least one of the plurality of in vivo medical devices, further comprises:

receiving the control signal at the first in vivo medical device;

generating a second control signal at the in vivo medical device; and transmitting the second control signal over the communication path between the first in vivo medical device and a second in vivo medical device to the second in vivo medical device.

* * * * *